United States Patent [19]

Berg

[11] Patent Number: 4,851,087
[45] Date of Patent: Jul. 25, 1989

[54] SEPARATION OF M-DIISOPROPYLBENZENE FROM P-DIISOPROPYL BENZENE BY AZEOTROPIC DISTILLATION WITH NITROGENOUS COMPOUNDS

[75] Inventor: Lloyd Berg, 1314 S. Third Ave., Bozeman, Mont. 59715

[73] Assignee: Lloyd Berg

[21] Appl. No.: 276,918

[22] Filed: Nov. 28, 1988

[51] Int. Cl.$^4$ ............................ B01D 3/38; C07C 7/06
[52] U.S. Cl. ........................................ 203/57; 203/58; 203/59; 203/60; 203/62; 203/63; 585/860; 585/862; 585/864; 585/865
[58] Field of Search ........................ 203/57, 58, 59, 60, 203/63, 62, 50; 585/808, 807, 804, 860, 862, 864, 865, 861

[56] References Cited

U.S. PATENT DOCUMENTS

| | | | |
|---|---|---|---|
| 2,290,636 | 7/1942 | Deanesly | 203/57 |
| 2,461,993 | 2/1949 | McKinnis | 203/62 |
| 2,805,258 | 9/1957 | Boodman et al. | 585/839 |
| 2,909,576 | 10/1959 | Fenske et al. | 585/861 |
| 3,132,078 | 5/1964 | Backlund | 203/58 |
| 3,222,349 | 12/1965 | Holder | 585/804 |
| 4,128,594 | 12/1978 | Westernacher | 585/806 |

FOREIGN PATENT DOCUMENTS

| | | | |
|---|---|---|---|
| 49-47326 | 5/1974 | Japan | 585/866 |
| 50-70324 | 6/1975 | Japan | 585/864 |
| 804221 | 12/1958 | United Kingdom | 585/860 |

Primary Examiner—Wilbur Bascomb

[57] ABSTRACT

Meta and para-diisopropylbenzenes cannot be easily separated from each other by distillation because of the closeness of their vapor pressures. m-Diisopropylbenzene can be readily removed from p-diisopropylbenzene by azeotropic distillation using certain nitrogenous compounds. Typical effective azeotropic distillation agents are ethanolamine and benzonitrile.

10 Claims, No Drawings

SEPARATION OF M-DIISOPROPYLBENZENE FROM P-DIISOPROPYL BENZENE BY AZEOTROPIC DISTILLATION WITH NITROGENOUS COMPOUNDS

This application is related to co-pending application Ser. No. 07/270,200 filed on Nov. 14, 1988 related to the same separation of m-diisopropylbenzene from p-diisopropylbenzene using different agents.

FIELD OF THE INVENTION

This invention relates to a method for separating m-diisopropylbenzene from p-diisopropylbenzene using certain nitrogenous compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates or effect the same separation or make possible a greater degree of separation with the same number of plates. The azeotrope forming agent is introduced with the feed to a continous column. The azeotrope forming agent and the more volatile component are taken off as overhead product and the less volatile compound comes off as bottoms product. The usual methods of separating the azeotrope former from the more volatile component are cooling and phase separation or solvent extraction.

In the manufacture of cumene, also called isopropylbenzene, by the alkylation of benzene with propylene, the most prevalent by-products are the diisopropylbenzenes with the meta and para isomers comprising most of the by-product. m-Diisopropylbenzene (m-DIPB) boils at 203.2° C. m-Diisopropylbenzene (p-DIPB) boils at 210.3° C. and these two have a relative volatility of 1.14. The difficulty of separating these two by rectification can be shown by the data in Table 1. Table 1 shows

TABLE 1

| Plates Required To Effect Separation In 99% Purity | | |
| --- | --- | --- |
| Relative Volatility | Theoretical Plates | Actual Plates, 75% Efficiency |
| 1.14 | 71 | 95 |
| 1.22 | 47 | 63 |
| 1.25 | 41 | 55 |
| 1.29 | 36 | 48 | that rectification of m-DIPB from p-DIPB in 99% purity requires 95 actual plates. Using azeotropic distillation with an agent yielding a relative volatility of 1.29 would require only 48 actual plates. Thus azeotropic distillation would be an attractive method of effecting the separation of these isomers if agents can be found that (1) will increase the relative volatility of m-DIPB to p-DIPB and (2) are easy to recover from the p-DIPB. Azeotropic distillation typically requires the addition of about as much agent as m-DIPB to be boiled up in the column which increases the heat requirement as well as somewhat larger diameter plates to accomodate the increase of liquid and vapor in the column. In addition, a solvent extraction column is usually provided to recover and recycle the azeotrope forming agent.

OBJECTIVE OF THE INVENTION

The objective of this invention is to provide a process or method of azeotropic distillation that will enhance the relative volatility of m-DIPB from p-DIPB in their separation in a rectification column. It is a further object of this invention to identify organic compounds which in addition to the above constraints, are stable, can be separated from m-DIPB by solvent extraction and can be recycled to the azeotropic distillation and reused with little decomposition.

SUMMARY OF THE INVENTION

The objects of this invention are provided by a method for separating m-DIPB from p-DIPB which entails the use of certain nitrogenous compounds in an azeotropic distillation process.

DETAILED DESCRIPTION OF THE INVENTION

I have discovered that certain nitrogenous compounds will effectively enhance the relative volatility of m-DIPB from p-DIPB and permit the separation of m-DIPB from p-DIPB by rectification when employed as the agent in azeotropic distillation. Table 2 lists the nitrogenous compounds that I have found to be effective.

TABLE 2

| Effective Azeotrope Forming Agents - Nitrogenous Compounds | | |
| --- | --- | --- |
| Compound | Azeotrope, B.P., °C. | Relative Volatility |
| N—(2-Hydroxyethyl)-2-pyrrolidone | 200 | 1.40 |
| 2-Nitrotoluene | 198 | 1.27 |
| Ethanolamine | 157 | 1.27 |
| Benzonitrile | 195 | 1.26 |
| Diethylene triamine | 188 | 1.25 |
| Aniline | 178 | 1.25 |
| 2-Methyl pentamethylene diamine | 185 | 1.23 |
| N—Methyl ethanolamine | 153 | 1.19 |
| Nitrobenzene | 190 | 1.18 |

The nitrogenous compounds which are effective are 2-nitrotoluene, N-(2-hydroxyethyl)-2-pyrrolidone, ethanolamine, benzonitrile, diethylene triamine, aniline, 2-methyl pentamethylene diamine, N-methyl ethanolamine and nitrobenzene. For example, the data in Table 2 indicates that one part of ethanolamine mixed with one part of m-DIPB - p-DIPB mixture gives a relative volatility of 1.27.

THE USEFULNESS OF THE INVENTION

The usefulness or utility of this invention can be demonstrated by referring to Tables 1 and 2. All of the successful azeotropic agents show that m-DIPB can be separated from p-DIPB by means of distillation in a rectification column and that ease of separation as measured by relative volatility is considerable. Without these azeotropic agents, only slight improvement will occur in a rectification column.

WORKING EXAMPLES

Example 1

Forty grams of m-DIPB - p-DIPB mixture and 40 grams of N-(2-hydroxyethyl)-2-pyrrolidone were charged to an Othmer type vapor-liquid equilibrium still and refluxed for three hours. Analysis by gas chromatography gave a vapor composition of 66.2% m-DIPB, 33.8% p-DIPB; a liquid composition of 60% m-DIPB, 40% p-DIPB. This indicates a relative volatility of m-DIPB to p-DIPB of 1.40.

Example 2

Forty grams of m-DIPB - p-DIPB mixture and 40 grams of 2-nitrotoluene were charged to the vapor-liquid equilibrium still and refluxed for an hour. Analysis indicated a vapor composition of 67.3% m-DIPB, 32.7% p-DIPB; a liquid composition of 61.8% m-DIPB, 38.2% p-DIPB which is a relative volatility of 1.27.

Example 3

A two foot long rectification column packed with Berl saddles was calibrated with m-DIPB and p-DIPB which possesses a relative volatility of 1.14 and found to have 2.3 theoretical plates. A solution comprising 50 grams of m-DIPB, 50 grams p-DIPB and 30 grams of benzonitrile was placed in the stillpot and heated. After two hours of refluxing at total reflux, analysis was made by gas chromatography. The overhead composition was 66.7% m-DIPB, 33.3% p-DIPB and the stillpot analysis was 53.8% m-DIPB, 46.2% p-DIPB. Using these compositions in the Fenske equation with the theoretical plates in the column being 2.3, gave an average relative volatility of 1.26 for each theoretical plate.

I claim:

1. A method for recovering m-diisopropylbenzene from a mixture of m-diisopropylbenzene and p-diisopropylbenzene which comprises distilling a mixture of m-diisopropylbenzene and p-diisopropylbenzene in a rectification column in the presence of an azeotrope forming agent, recovering the m-diisopropylbenzene and the azeotrope forming agent as overhead product, obtaining the p-diisopropylbenzene from the stillpot, wherein said azeotrope forming agent is a nitrogen containing organic compound which forms a minimum boiling azeotrope with m-diisopropylbenzene, said azeotrope having a volatility relative to p-diisopropylbenzene in the range of 1.18 to 1.40.

2. The method of claim 1 in which the azeotrope forming agent is N-(2-hydroxyethyl)-2-pyrrolidone.

3. The method of claim 1 in which the azeotrope forming agent is 2-nitrotoluene.

4. The method of claim 1 in which the azeotrope forming agent is ethanolamine.

5. The method of claim 1 in which the azeotrope forming agent is benzonitrile.

6. The method of claim 1 in which the azeotrope forming agent is diethylene triamine.

7. The method of claim 1 in which the azeotrope forming agent is aniline.

8. The method of claim 1 in which the azeotrope forming agent is 2-methyl pentamethylene diamine.

9. The method of claim 1 in which the azeotrope forming agent is N-methyl ethanolamine.

10. The method of claim 1 in which the azeotrope forming agent is nitrobenzene.

* * * * *